(12) United States Patent
Nakano et al.

(10) Patent No.: US 9,441,031 B2
(45) Date of Patent: Sep. 13, 2016

(54) ORIENTED COLLAGEN/APATITE MATERIAL AND METHOD FOR PRODUCING ORIENTED COLLAGEN/APATITE MATERIAL

(75) Inventors: Takayoshi Nakano, Suita (JP); Aira Matsugaki, Suita (JP); Takuya Ishimoto, Suita (JP); Taro Saku, Yamatokouriyama (JP); Yoshihiro Isobe, Yamatokouriyama (JP)

(73) Assignee: ATREE, INC. (JP)

( * ) Notice: Subject to any disclaimer, the term of this patent is extended or adjusted under 35 U.S.C. 154(b) by 128 days.

(21) Appl. No.: 13/825,787

(22) PCT Filed: Sep. 15, 2011

(86) PCT No.: PCT/JP2011/005203
§ 371 (c)(1),
(2), (4) Date: Apr. 9, 2013

(87) PCT Pub. No.: WO2012/039112
PCT Pub. Date: Mar. 29, 2012

(65) Prior Publication Data
US 2013/0190480 A1    Jul. 25, 2013

(30) Foreign Application Priority Data
Sep. 22, 2010  (JP) ................. 2010-211598

(51) Int. Cl.
| | |
|---|---|
| A61L 27/12 | (2006.01) |
| A61L 27/32 | (2006.01) |
| A61L 15/32 | (2006.01) |
| C07K 14/78 | (2006.01) |
| A61L 27/46 | (2006.01) |
| A61L 27/24 | (2006.01) |
| A61L 27/28 | (2006.01) |
| A61L 27/38 | (2006.01) |
| A61K 38/00 | (2006.01) |

(52) U.S. Cl.
CPC ............. *C07K 14/78* (2013.01); *A61L 27/12* (2013.01); *A61L 27/24* (2013.01); *A61L 27/28* (2013.01); *A61L 27/3821* (2013.01); *A61L 27/46* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 5,532,217 A | 7/1996 | Silver et al. | |
| 6,387,414 B1 | 5/2002 | Akashi et al. | |
| 7,547,449 B2* | 6/2009 | Gower et al. | 424/426 |
| 2004/0101960 A1 | 5/2004 | Schaefer et al. | |
| 2005/0053638 A1* | 3/2005 | Tanaka et al. | 424/423 |
| 2005/0147612 A1* | 7/2005 | Yayon et al. | 424/146.1 |
| 2007/0031465 A1 | 2/2007 | Kojima et al. | |
| 2008/0033550 A1 | 2/2008 | Taira | |
| 2008/0208550 A1* | 8/2008 | Ascenzi | 703/11 |
| 2010/0074874 A1 | 3/2010 | Torbet et al. | |
| 2011/0033552 A1* | 2/2011 | Shoji | 424/499 |

FOREIGN PATENT DOCUMENTS

| | | |
|---|---|---|
| CN | 101554493 A | 10/2009 |
| EP | 1902739 | 3/2008 |
| JP | 10-127753 | 5/1998 |
| JP | 11-319068 | 11/1999 |
| JP | 2000-327314 | 11/2000 |
| JP | 2005-278909 | 10/2005 |
| JP | 2006-20222 | 10/2008 |
| JP | 2010-504122 | 2/2010 |
| JP | 2010-148691 | 7/2010 |
| JP | 2010167274 A | 8/2010 |
| JP | 2012-500203 | 1/2012 |
| WO | WO-0137889 | 5/2001 |
| WO | WO-2004041320 | 5/2004 |
| WO | WO-2005035014 | 4/2005 |
| WO | WO-2008034854 A1 | 3/2008 |
| WO | WO-2008-157594 | 12/2008 |
| WO | WO-2009-084507 | 7/2009 |
| WO | WO-2010-019625 | 2/2010 |
| WO | WO-2010-095427 | 8/2010 |
| WO | WO-2010-101639 | 9/2010 |

OTHER PUBLICATIONS

Tampieri et al. (2003) Biologically inspired synthesis of bone-like composite: self-assembled collagen fibers/hydroxyapatite nanocrystals, J. Biomed. Mater. Res. A, vol. 67, No. 2, pp. 618-625.*
Bandyopadhyay-Ghosh S. (2008) Bone as a Collagen-hydroxyapatite Composite and its Repair, Trens Biomater. Artif. Organs, vol. 22, No. 2, pp. 116-124.*
Wahl et al. (2006) Collagen-Hydroxyapatite Composites for Hard Tissue Repair, Eur. Cell. Mater., vol. 11, pp. 43-56.*

(Continued)

*Primary Examiner* — Anand Desai
*Assistant Examiner* — Samuel Liu
(74) *Attorney, Agent, or Firm* — ALG Intellectual Property, LLC

(57) ABSTRACT

It is an object of the present invention to provide an oriented collagen/apatite material wherein an orientation is controlled, and a method of the oriented collagen/apatite material wherein an orientation is controlled. A method of producing an orientated collagen/apatite material according to the present invention, is characterized in that the method comprises; preparing a collagen having an orientation, seeding an osteoblast or a mesenchymal stem cell to produce and fix an apatite having an orientation similar to or almost the same as a direction of an orientation of the collagen on a surface and/or inside of the collagen. Furthermore, in a preferred embodiment of above mentioned method of producing an orientated collagen/apatite material according to the present invention, is characterized in that the osteoblast is an osteoblast like cell or an osteoblast obtained from a living organism.

6 Claims, 5 Drawing Sheets

(56) References Cited

OTHER PUBLICATIONS

Du et al. (1999) Three-dimensional nano-HAp/collagen matrix loading with osteogenic cells in organ culture, J. Biomad. Mat. Res., vol. 44, issue 4, pp. 407-415.*
Sigma-Aldrich catalog (2015) Sodium phosphate dibasic, p. 1-3.*
Nakamura et al. (1991) Oriented Collagen Matrices: the Control of Biomineralizaton in Bone, Mat. Res. Soc. Symp. Proc., vol. 218, pp. 275-280.*
Ibusuki et al. (1999) Photochemically Cross-Linked Collagen Gels as Three-Dimensional Scaffolds for Tissue Engineering, Tissue Eng., vol. 13, pp. 1995-2001.*
Jim Torbet et al., Orthogonal scaffold of magnetically aligned collagen lamellae for corneal stroma reconstruction, Mar. 6, 2007.
Chizuru Hongo et al., "Bunshi Haiko o Seigyo Shita Sekisoka Collagen Gel no Sosei," The Society of Polymer Science Japan, V. 37, 2008, p. 65-66.
Chizuru Hongo et al., Development of Collagen Hydrogel with High Mechanical Strength by a Simple Orientation Method for Triple-helix, Chemistry Ltrs, vol. 37, No. 12, p. 1254-55.
Mitsuru Akashi et al., "Kakumaku Jisshitsu Saisei o Mokuteki to Shita Haiko Sekisogata Collagen Gel no Sosei," Kuntan Kenkyu Kokokkusha, 2008, pp. 9-12.
Joelito Razal et al., Arbitrarily Shaped Fiber Assemblies from Spun Carbon Nanotube Gel Fibers, 2007.
Chizuru Hongo et al., "Bunshi Halko o Seigyo Shita Sekisoka Collagen Gel no Sosei," The Society of Polymer Science Japan, V. 37, 2008, p. 65-66.
Mitsuru Akashi et al., "Kakumaku Jisshitsu Saisei o Mokuteki to Shita Haiko Sekisogata Collagen Gel no Sosei," Kuntan Kenkyu Kokokkusha, 2008, pp. 9-12.
Y. Tanaka et al., "Fabrication of multilayered collagen hydrogels . . . ," Japanese Society for Biomaterials Symposium Yokoshu, 2008, vol. 2008, p. 138.
Chizuru Hongo et al., "Bunshi Haiko o Seigyo Shita Sekisoka Collagen Gel no Sosei to Kakumaku . . . ," Japanese Society for Biomaterials Symposium, 2008, vol. 2008, p. 139.
Masato Kukizaki et al., "Nano Bubble no Seisei to Kihokei no Seigyo," Miyazaki Pprefecture Industrial Technology Center, Hokoku, 2004, No. 48, pp. 13-16.
Tetsushi Taguchi et al., Hydroxyapatite Formation on/in Poly(vinyl alcohol) Hydrogel Natrices Using a Novel Alternate Soaking Process, Apr. 16, 1998.
Masanori Kikuchi et al., Self-organization mechanism in a bone-like hydroxyapatite/collagen nanocomposite synthesized in vitro and its biological reacttion in vivo. Oct. 8, 2000.
Shinohara Hajime et al., The Journal of Physical Medicine, Nov. 30, 2008, vol. 19.
Taro Takeuchi et al., Abstracts of the Japan Institute of Metals, Sep. 15, 2009, vol. 145th.
Y. Yokogawa et al., Calcium Phosphate Formation on Highly-oriented Collagen Fibrls, Chem. Lett., No. 6, Jun. 5, 1999.
Aira Matsugaki et al., Abstracts of the Japan Institute of Metals, Sep. 25, 2010, vol. 147th.
Search Report and Written Opinion received in International Application No. PCT/JP2011/005203; Nov. 1, 2011.
EA Office Action, Dec. 4, 2014, issued in related Patent Application No. PCT/JP2011/005203.

* cited by examiner

ORIENTED COLLAGEN/APATITE MATERIAL AND METHOD FOR PRODUCING ORIENTED COLLAGEN/APATITE MATERIAL

TECHNICAL FIELD

The present invention relates to an oriented collagen/apatite material, and a method of producing the oriented collagen/apatite material, in particular, an oriented collagen/apatite material and a method of producing the oriented collagen/apatite material, using a collagen having an orientation.

BACKGROUND

In the past, a non orientated collagen was used as a substrate material of a cell culture for many years. On the contrary, although a collagen having an orientation is found in tremendous numbers in the human body, a collagen/apatite of a bone is also orientated according to the site of the bone, it has been thought that the orientation of a collagen/apatite plays a role in functions of growth and strength etc., of a bone.

As a method of a collagen substrate having an orientation, it is generally known a method of applying a powerful magnetic field to it during a process of formation of a collagen fiber (JP-A-2006-280222, "Patent Literature 1"). Further, it is also known a method of spin-coating a collagen gel (JP-A-2010-148691, "Patent Literature 2").

Further, as a method of producing a hard tissue of a living organism which resembles a bone etc., by calcifying a collagen, a method of seeding an osteoblast is generally known (JP-A-2005-278909, "Patent Literature 3").

As a method of synthesizing a hydroxyapatite which is known as a main component of a bone or a tooth other than the method of seeding an osteoblast, a method of dipping a substrate such as high-polymer materials to calcium solution and phosphoric acid solution alternately is suggested (JP-A-2000-327314, "Patent Literature 4;" T. Taguchi, A. Kishida, M. Akashi, Hydroxyapatite Formation on/in Poly (vinyl alcohol) Hydrogel Matrices using a Novel Alternate Soaking Process(I), Chem. Lett., pp. 711-712, 1998, "Nonpatent Literature 1").

Furthermore, as a method of controlling an orientation of apatite, a method of producing a collagen/apatite complex according to a simultaneous titration coprecipitation method is suggested (JP-A1-2004-041320, "Patent Literature 5;" M. Kikuchi, S. Ito, S. Ichinose, K. Shinomiya, J. Tanaka. Self-organization mechanism in a bone-like hydroxyapatite/collagen nanocomposites synthesized in vitro and its biological reaction in vivo, Biomaterials, Vol. 22, pp. 1705-1711, 2001, "Nonpatent Literature 2").

SUMMARY

However, in the past, although there are techniques for orientating a single substance of a collagen as described in the above Patent Literatures 1 and 2, it is impossible to produce an oriented collagen/apatite material which an orientation is controlled. Further, an orientation according to the above Patent Literature 3 is not controlled. Further, although it is thought that the above Patent Literature 4 relates to a self-organizing reaction known in the past, there are no attempt regarding a production of an orientated material according to this method in both a micro order and a macro order.

In this manner, although there are techniques for orientating a collagen in the past, there are no techniques of producing a calcified collagen at a macro size of a milli order or more. As a result of this, there are no materials capable of using practically which have an oriented collagen/apatite similar to a bone which is oriented according to a site.

Therefore, it is an object of the present invention to provide an oriented collagen/apatite material wherein an orientation is controlled, and a method of the oriented collagen/apatite material wherein an orientation is controlled.

In order to accomplish the above object, the present inventors made strenuous studies as to an orientation of a collagen and an apatite having an orientation. As a result, the inventors discovered the present inventions.

That is, a method of producing an orientated collagen/apatite material according to the present invention, is characterized in that the method comprises preparing a collagen having an orientation, seeding an osteoblast or a mesenchymal stem cell to produce and fix an apatite having an orientation similar to or almost the same as a direction of an orientation of the collagen on a surface and/or inside of the collagen.

Furthermore, in a preferred embodiment of above mentioned method of producing an orientated collagen/apatite material according to the present invention, is characterized in that the osteoblast is an osteoblast like cell or an osteoblast obtained from a living organism.

Furthermore, in an another embodiment of a method of producing an orientated collagen/apatite material according to the present invention, is characterized in that the method comprises preparing a collagen having an orientation, immersing the collagen into a solution containing calcium ion and essentially no phosphate ion and a solution containing phosphate ion and essentially no calcium ion alternately to produce and fix an apatite having an orientation similar to or almost the same as a direction of an orientation of the collagen on a surface and/or inside of the collagen.

Furthermore, in a preferred embodiment of a method of producing an orientated collagen/apatite material according to the present invention, is characterized in that the solution containing calcium ion and essentially no phosphate ion is calcium chloride solution, calcium acetate solution, tris buffer solution of calcium chloride, tris buffer solution of calcium acetate or a mixed solution thereof.

Furthermore, in a preferred embodiment of a method of producing an orientated collagen/apatite material according to the present invention, is characterized in that the solution containing phosphate ion and essentially no calcium ion is sodium hydrogenphosphate solution, sodium ammonium dihydrogenphosphate solution, tris buffer solution of sodium hydrogenphosphate, tris buffer solution of sodium ammonium dihydrogenphosphate or a mixed solution thereof.

Furthermore, an orientated collagen/apatite material according to the present invention, is characterized in that the material comprises a collagen having an orientation, an apatite produced and fixed on a surface and or in inside of the collagen which has an orientation similar to or almost the same as a direction of an orientation of the collagen.

Furthermore, in a preferred embodiment of an orientated collagen/apatite material according to the present invention, is characterized in that the orientation is an uniaxial orientation, a spiral orientation, a double axis orientation, a two-dimensional orientation, a triaxial orientation, or a three-dimensional orientation.

Furthermore, in a preferred embodiment of an orientated collagen/apatite material according to the present invention, is characterized in that a size of the material is a macro size of a millimeter order or more.

Furthermore, in a preferred embodiment of an orientated collagen/apatite material according to the present invention, is characterized in that the collagen having an orientation is coated on a substrate comprising a metal, a ceramics, a high-polymer material or a biomaterial.

Furthermore, in a preferred embodiment of an orientated collagen/apatite material according to the present invention, is characterized in that in the material, a calcification is generated by the deposition of the apatite on a surface and/or inside of the collagen.

The present invention has an advantage effect that it is possible to make and control an orientation of a collagen/apatite at a macro size of a millimeter order or more. Further, the present invention has an advantage effect that it is possible to produce a biocompatible material which an orientation is controlled so that the orientation can be nearly equal to an orientation of each site of a normal hard tissue of a living organism, since a hard tissue has an orientation of a collagen/apatite according to a site of a hard tissue.

For example, it is thought that an orientation in a bone tissue plays a role in an intensity in a specified direction. Although a femur has a C axis orientation of a collagen/apatite along the line with a long axis of a bone, in the case that a bony defect at a macro size is occurred, it is needed for a long time to recover an original orientation, and it is very difficult to recover an orientation which a bone tissue has originally. However, it is expected that an insertion of an orientated material at a macro size of a millimeter order or more obtained by the present invention which an orientation is controlled, according to an original orientation of a bone makes it possible to produce an early success of osteoanagenesis and an original orientation.

Furthermore, on going the way to an aging society, the sharp increase of a bone disease such as osteoporosis or arthrosis deformans makes a high expectations for a regeneration medicine of a bone. However, it is impossible to explain it using only a change of a bone density which has been measured at a medical field in the past, in an intensity and function of a bone and a bone metabolism cycle which repeats a dissolution and a regeneration. Therefore, an orientation of an apatite attracts attention as a parameter of a quality of bone when a function of bone is decided. A method of producing an orientated collagen/apatite material and the material thereof according to the present invention has an advantage effect that it is possible to produce not only an orientated collagen/apatite material wherein an orientation is controlled for a research and development of a basic medical for future bony medical services, but a biocompatible material suitable for practical use in a field of osteoanagenesis.

DESCRIPTION OF EMBODIMENTS

Figure 1:
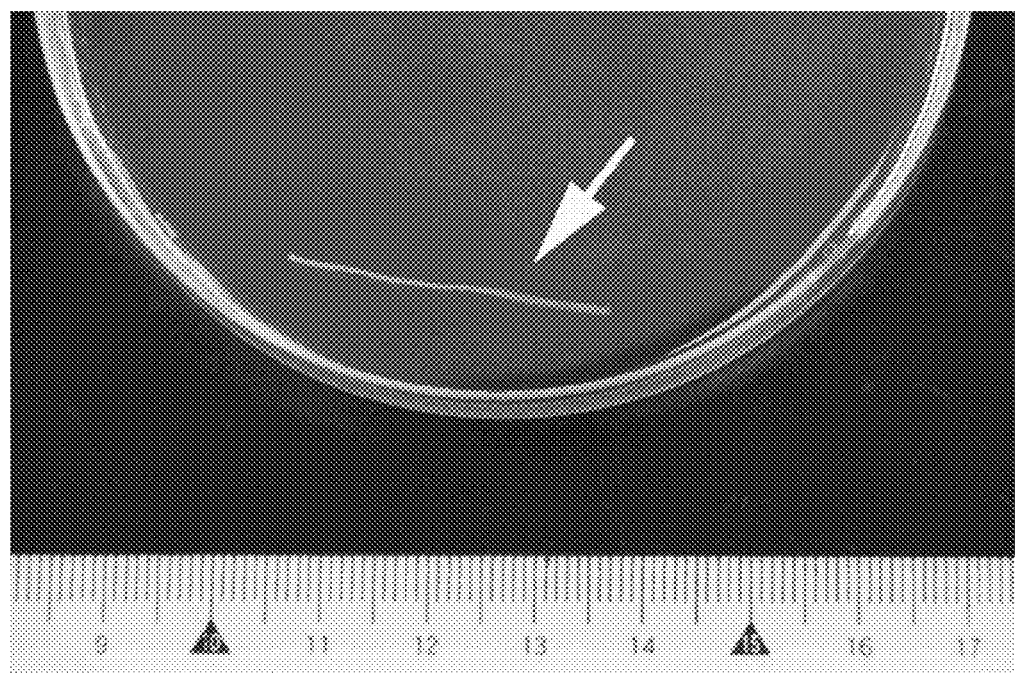
FIG. 1 gives a photograph of a collagen gel having an orientation immediately after it is produced in a PBS.

It is possible to produce an orientated collagen/apatite material according to the present invention mainly by a method of preparing a collagen (substrate) having an orientation and seeding an osteoblast or a mesenchymal stem cell, or a method of preparing a collagen (substrate) having an orientation and immersing the collagen into a calcium ion solution and phosphate ion solution, or a method according to SBF (simulated body fluid) immersing.

In any method, it is possible to produce and fix an apatite having an orientation similar to or almost the same as a direction of an orientation of the collagen (substrate) on the collagen (substrate) or on a surface and/or inside of the collagen, at a macro size of a millimeter order or more.

At first, a method of seeding an osteoblast etc., will be explained. A method of producing an orientated collagen/apatite material according to the present invention, is characterized in that the method comprises preparing a collagen having an orientation, seeding an osteoblast or a mesenchymal stem cell to produce and fix an apatite having an orientation similar to or almost the same as a direction of an orientation of the collagen on the collagen, or a surface and/or inside of the collagen.

First of all, an explanation as to a collagen having an orientation is as follows. A collagen having an orientation means a collagen which a travel direction of a fibrous collagen such as a single collagen gel or a dry collagen gel uniforms in some direction. In the case that a collagen having an orientation is coated in a substrate comprising a metal, a ceramics, a high-polymer material or a biomaterial (hereinafter it is a collagen substrate), a collagen having an orientation means a collagen which a travel direction of a fibrous collagen such as a single collagen gel or a dry collagen gel coated on a substrates such as a metal, a ceramics, a high-polymer material or a biomaterial formed to various shapes, uniforms in some direction.

Further, an orientation of an apatite means a produced apatite which a crystal structure of an apatite uniforms in some direction. A biological apatite which is one of an object of application of the present inventions, is an ionic crystal having a strong anisotropy with a base unit of a crystal structure similar to a hexagonal column defined by a axis and c axis, and it is known that c axis of a biological apatite almost uniforms in a travel direction of a fibrous collagen. In the present invention, it is preferable that c axis of a produced apatite is similar to or almost the same as a travel direction of a fibrous collagen.

An advantage of the use of a collagen having an orientation as a starting material is as follows. That is, the reasons is that the use of a collagen having an orientation in a curve within a collagen as a stating material makes it possible to also produce an orientation in a curve in an osteoblast. Further, in the present invention, it is essentially possible to develop an osteoblast with an orientation at a "surface" of collagen (substrate), although it is also thought that an osteoblast gets into inside of a collagen (substrate), it is possible to include such cases in the present invention. Furthermore, according to the present invention, if an orientated collagen having some shape and some direction of an orientation as a starting material is prepared depending on a needs of an orientated material as an end product, it is possible to produce an orientated collagen/apatite with a larger size than a millimeter order by controlling a shape or a direction of an orientation without any inhibition.

A method of preparing a collagen having an orientation is not particularly limited, but according to a common procedure. For example, as a method of giving an orientation to a collagen at a larger size than a millimeter order, a method of giving a flow of a fixed direction to collagen solution during a process of gelating a collagen solution is suggested, but other method may be used. As other method, mention may be made of a method of applying a strong magnetic field during a process of forming a collagen fiber, a method of spin-coating a collagen gel, a method of drawing a collagen gel to a predetermined direction mechanically (and physically).

In the case that a collagen gel having an orientation is prepared by a method of applying a strong magnetic field during a process of forming a collagen fiber, since a collagen fiber is set in array in a perpendicular direction to the magnetic field, if it is kept to apply a magnetic field from the same direction, it is possible to obtain a two-dimensional orientation, and if it is kept to apply a rotational magnetic field, it is possible to obtain a single axis orientation. It is possible to use a method of applying a magnetic field if such collagen having an orientation is used as a starting material. However, if the magnetic field is used, basically, it is possible to produce only those of the collagen having a uniform orientation, and a macro shape also tends to be limited. On the other hand, in the case that a collagen gel having an orientation is prepared by a method of giving a flow of a fixed direction to collagen solution during a process of gelating a collagen solution. it is possible to produce a collagen having a different 3D orientation by forming and laminating a various shape including a sheet-like shape because of the use of a flow of liquid.

As mentioned after, a prepared orientated collagen (single collagen) in the example can be obtained by using a flow of a collagen solution to give an orientation to a collagen during a process of obtaining a collagen gel. Although it is a string-shaped of a collagen in the photograph of the example, it is possible to produce an orientated collagen or a collagen substrate with various shapes (line, plane, three dimension) such as a ribbon-shaped with a large width. Further, during a process, a control of a velocity of a flow also makes it possible to control a degree of the orientation. Therefore, since it is possible to control a direction of the orientation or a degree of the orientation thereby giving a desired distribution, the use of such collagen or collagen substrate according to the present invention also makes it possible to control a direction of the orientation and a degree of the orientation (that is control of distribution of the orientation) regarding an orientation of an apatite.

For example, an explanation as to a method of giving a flow of a fixed direction to collagen solution during a process of gelating a collagen solution is as follows. Although a concentration of a collagen solution is preferably 10 mg/mL or more form a viewpoint that an obtained collagen or a collagen substrate can have an enough mechanical strength, it may be about 3 mg/mL or more. An origin of a collagen is not limited. Further, a seed, a site of a tissue, an age etc., of an animal derived from are not particularly limited. For example, it is possible to use one derived from animals such as a rat tail, a pig hide, a cowskin (including a fatty deposit). That is, it is possible to use a collagen obtained from a skin, a bone, a cartilage, a tendon, an internal organ of a mammal (for example, such as a cattle, a pig, a horse, a rabbit, a mouse etc.) or birds (for example, chicken etc.).

A collagen like protein derived from a skin, a bone, a cartilage, a fin, a fish scale, an internal organ of fishes (for example, such as a pacific cod, a paralichthys olivaceus, a flatfish, a salmon, a trout, a tuna, a chub mackerel, a sea bream, a sardine, a shark etc.) may be used. Moreover, a method of extracting a collagen is not particularly limited, but a common method of extracting may be used. Further, a collagen obtained by a recombinant DNA technique other than that from the extraction from an animal tissue, may be used. Further, in order to suppress an antigenecity, an enzyme-treated atelocollagen may be used. Further, as a collagen, an unmodified soluble collagen such as an acid soluble collagen, a salt soluble collagen, an enzyme soluble collagen (atelocollagen), a chemically-modified collagen such as acylation such as succinylation, phthalation, esterification such as methylation, deamination of alkali solubilization, and further an insoluble collagen such as a tendon collagen etc., may be used.

It is possible to quantitatively assess a direction of an orientation or a degree of an orientation as to an obtained collagen by using, for example, a raman spectroscopy microscope. A raman spectroscopy is to examine a component which a frequency modulation of a scattered light caused by hitting against molecular is occurred according to molecular vibration, by means of the use of a spectroscope, and thereby making it possible to obtain information as to a composition of a target for analysis or a crystal structure to analysis an orientation of collagen.

For a collagen having an orientation obtained thus, an osteoblast or a mesenchymal stem cell is seeded to produce and fix an apatite having an orientation similar to or almost the same as a direction of an orientation of the collagen on the collagen. In a preferred embodiment, the osteoblast is an osteoblast like cell or an osteoblast obtained from a living organism. As a cell other than these, a osteoblast which is differentiated from a mesenchymal stem cell isolated from a bone marrow, an odontoblast, or an ameloblast may be used (a cell may be used which can differentiate to a hard tissue, that is a cell capable of calcifying may be used.). As an osteoblast like cell, it is possible to use an osteoblast like cell MC3T3-E1. Moreover, for an osteoblast like cell, it is possible to use an osteoblast committed stem cell strain established from a skullcap of C57BL/6 newborn mouse (which is the same osteoblast, but there is a difference whether or not it is a primary culture or cell strain.). As an osteoblast like cell other than these, it is possible to use a mouse MC3T3-E1, a human Saos-2, a MG63, a rat UMR106, a ROS17/2.8 etc. Moreover, MC3T3-E1 is an osteoblast committed stem cell strain established from a skullcap of C57BL/6 newborn mouse. MC3T3-E1 is one of a cell strain used for a differential model of the osteoblast. Although there are some cell strain such as those derived from a human or a rat as described above, but those may be used. The present inventions make it possible to seed an osteoblast or a mesenchymal stem cell etc., to a collagen having an orientation to grow the osteoblast or the mesenchymal stem cell up having an orientation in a surface, or inside of the collagen when the osteoblast gets into inside of the collagen.

As a culture of the osteoblast, it is possible to use a MEM-α serum medium basically, and to be carried out at 37° C. under the condition of 5% $CO_2$ for about 24 hours. There is a possibility that some of the osteoblast become a bone cell with a low activity caused by entering into a calcified site in a culture cell. Moreover, it is thought that there is no osteoblast because of the use of a cultured system of the osteoblast, but there are some contaminations of an osteoclast, a bone cell, a fibrocyte etc., in a primary culture. Therefore, it is possible to contain an osteoclast, a bone cell, a fibrocyte etc., in a culture medium.

Moreover, an explanation as to a resource of phosphoric acid which is a component of the apatite, in the orientated collagen/apatite material is as follows. As a resource of phosphoric acid, in a culture condition, it is possible to add glycerophosphoric acid, β glycerophosphoric acid etc., to the medium. Such glycerophosphoric acid can become a resource of phosphoric acid during a calcification. This is further degraded by an ALP to become inorganic phosphoric acid.

Moreover, a differentiated osteoclast produces a collagen (the production of a collagen and followed by the calcification.). An addition of ascorbic acid in a differential medium makes it possible to accelerate the production of collagen. That is, a cell on the collagen (substrate) can produce a collagen by itself other than those from the substrate.

At this moment, a simple explanation as to the calcification is as follows. There are two type of the calcification, that is, a collagen calcification and a heterotopic calcification (non collagen calcification). In the present invention, it is thought that a collagen calcification seems to occur because a calcific substance is confirmed wherein a fibrous deposition is observed with a calcium stain. An advantage of the calcification is to increase an intensity of an orientated material. A calcified orientated collagen material at a size of mm order is similar to a structure of bone, and further the calcification makes it possible to increase an intensity (for example, it's intensity is clear in the case that it is clipped with a tweezer), and therefore, it has an advantage in the case that it is installed into an organism.

In general, the deposition of a crystal of calcium phosphate (hydroxyapatite) to a substance of bone (which comprises a collagen and non-collagen protein) means a calcification, and thereby forming a bone tissue. According to another view, details are as follows. An osteoblast excretes a matrix vesicle proliferously. A matrix vesicle is a structure surround with a lipid bilayer of 40 to 200 nm. The matrix vesicle contains an enzyme and a physiologically active substance. The matrix vesicle is excreted at almost the same time as that of a formation of a high-molecular material such as a collagen fiber. A matrix vesicle trapped to a network of these substance can decide a site of the calcification. This matrix vesicle become a nucleus of a primary calcification, a crystal like structure of hydroxyapatite comes into existence from the matrix vesicle. A crystal like structure increases and thereby breaking a vesicle membrane. Further, a calcification extends over a vesicle membrane, and thereby becoming a calcified spherical body. A calcified spherical body grown in size arrives in around a collagen fine fiber. An area of a calcification expands through a collagen calcification proceeding in the line with a collagen fine fiber.

Although the details of a mechanism is unclear in the orientated material of the present invention, a calcification of a collagen occurs since the calcific substance is confirmed wherein a fibrous deposition is observed with a calcium stain. Although in an embodiment of the present invention, a calcification of a collagen occurs, it is though that both a calcification of a complex produced at this time, that is, a calcification occurred on a template of a collagen base, and a calcification for a produced collagen (what is calls, a collagen calcification in the original meaning) occur.

It is easily possible to evaluate a direction of an orientation and a degree of an orientation as to an apatite produced and fixed on a collagen, on a surface and/or inside of a collagen, with the use of, for example, a micro area X-ray diffraction. Moreover, since there are so many unexplained matter as to a direction of an orientation of a osteoblast and c axis array of an apatite, it is not thought that an (crystallographically) orientation of an apatite (as a calcific substance) is based on the reasons that a cell is orientated. However, in the present invention, as described after in the Example, it is possible to prove an orientation of an apatite of an orientated material with the use of a micro area X-ray diffraction.

Next, it will be explained as to a method wherein comprises; preparing a collagen having an orientation, immersing the collagen into a solution containing calcium ion and a solution containing phosphate ion alternately. A method of producing an orientated collagen/apatite material according to the present invention, is characterized in that the method comprises preparing a collagen having an orientation, immersing the collagen into a solution containing calcium ion and essentially no phosphate ion and a solution containing phosphate ion and essentially no calcium ion alternately to produce and fix an apatite having an orientation similar to or almost the same as a direction of an orientation of the collagen on the collagen, on a surface and/or inside of the collagen.

An explanation as to a collagen having an orientation can be referred to the above example using a osteoblast. At first, a collagen having an orientation can be prepared according to the explanation of the example using the osteoblast as described above. As a method of giving an orientation to a collagen at a larger size than a millimeter order, as described above, a method of giving a flow of a fixed direction to collagen solution during a process of gelating a collagen solution is suggested, but other method may be used. Concerning a preferable concentration, an origin etc., of a collagen solution, it also can be referred to the above mentioned method of producing an orientated collagen/apatite material by seeding an osteoblast.

In the embodiment, an alternate immerse is carried out by using a collagen having an orientation prepared by the above manner. In the preferable embodiment, the solution containing calcium ion and essentially no phosphate ion may be calcium chloride solution, calcium acetate solution, tris buffer solution of calcium chloride, tris buffer solution of calcium acetate or a mixed solution thereof. In the case that there is a phosphate ion, since a generation speed of a hydroxyapatite (hereafter it calls a HAP) tends to reduce, the solution containing calcium ion is preferably and generally a solution containing calcium ion and essentially no phosphate ion.

In the solution containing calcium ion and essentially no phosphate ion, a concentration of calcium ion is preferably 0.01 to 10 mol/L, particularly 0.1 to 1 mol/L, from a viewpoint of a generation speed and a generation efficiency of a HAp. A pH of a calcium solution is not particularly limited, but in the case of the use of tris buffer solution, preferably pH 6 to 10, more preferably pH 7.4.

Moreover, in a preferable embodiment, the solution containing phosphate ion and essentially no calcium ion can be sodium hydrogenphosphate solution, sodium ammonium dihydrogenphosphate solution, tris buffer solution of sodium hydrogenphosphate, tris buffer solution of sodium ammonium dihydrogenphosphate or a mixed solution thereof. In the case that there is a calcium ion, since a generation speed of a HAP tends to reduce, the solution containing phosphate ion is preferably and generally a solution containing phosphate ion and essentially no calcium ion.

In the solution containing phosphate ion and essentially no calcium ion, a concentration of phosphate ion is preferably 0.01 to 10 mol/L, particularly 0.1 to 1 mol/L, from a viewpoint of a generation speed and a generation efficiency of a HAp. A pH of a phosphate solution is not particularly limited, but in the case of the use of tris buffer solution, preferably pH 6 to 10, more preferably pH 7.4.

A combination of the calcium solution and the phosphate solution is not particularly limited, but for example, mention may be made of a combination of calcium chloride solution and sodium hydrogenphosphate solution, a combination of calcium acetate solution and sodium ammonium dihydrogenphosphate solution. In the calcium solution and the phosphate solution, other ion can exist in a scope which is not departed from a desired object of the present invention. However there are possibilities of the formation of tricalcium phosphate (TCP) in the case of the existence of magnesium ion ($Mg^{2+}$) of 2.5 mM or more).

A prepared collagen or a collagen substrate as mentioned above, can be carried out by being immersed to a calcium solution etc., for 10 seconds to 120 minutes, preferably 1 minute to 60 minutes, more preferably about 2 minutes, after that, and being washed in the ultrapure water for 5 seconds to 120 minutes, preferably about 30 seconds, and then it can be immersed to a phosphate solution etc., for 10 seconds to 120 minutes, preferably 1 minute to 60 minutes, more preferably about 2 minutes, and thereby washing in the ultrapure water for 5 seconds to 120 minutes, preferably about 30 seconds. As assuming that this is one cycle, it is possible to carry out 1 to 100 cycles, preferably 5 to 70 cycles, more preferably about 20 to 50 cycles. From a viewpoint that a calcification and an orientation is certainly carried out, it is possible to carry out about 10 cycles, about 30 cycles or more.

It is easily possible to evaluate a direction of an orientation and a degree of an orientation as to an apatite produced and fixed on a collagen (substrate), on a surface and/or inside of a collagen, with the use of, for example, a micro area X-ray diffraction.

In an another embodiment, a method of producing an orientated collagen/apatite material according to the present invention, is characterized in that the method comprises preparing a collagen having an orientation, coating an inside and/or a surface of the collagen with an apatite deposited by a simulated body fluid to produce and fix an apatite having an orientation similar to or almost the same as a direction of an orientation of the collagen on the collagen, a surface and/or inside of the collagen.

An explanation as to a collagen having an orientation can be referred to the above example using a osteoblast. In the present invention, a surface and/or inside of a collagen can be coated with an apatite deposited by a simulated body fluid. The term a surface here includes surfaces of a void or a gap existing in a collagen other than a specific overall surface of a collagen. An apatite may be coated in all of the surface or a part of the surface. A means of coating is not particularly limited to, but generally it is possible to be carried out by immersing a collagen into a simulated body fluid to deposit an apatite.

A simulated body fluid means a solution of a body fluid containing a salt, as a component of a salt, mention may be made of NaCl, $NaHCO_3$, KCl, $K_2HPO_4$, $MgCl_2$, $CaCl_2$, $Na_2SO_4$ etc. It is preferably a body fluid containing NaCl, $NaHCO_3$, $K_2HPO_4$, $CaCl_2$. A concentration of a salt of a simulated body fluid is in a range of a concentration of a normal body fluid to 10 times of the concentration. To a solution containing these salt is immersed a prepared collagen. The time of immersing can be 1 day or more. It is possible to coat a large amount of an apatite as the time passes. Although it can be carried out in a scope of 4 to 40° C. of a temperature of immersing, it is necessary to be carried out an immersion at a lower temperature than a denaturation temperature of the used collagen since there is a possibility of occurring a denaturation during immersing, depending on the variety of a collagen. It is possible to preferably coat at a temperature as long as high to terminate a coating at a short time.

Next, it will be explained from a viewpoint of a control of an orientation. In any cases of a method of seeding osteoblast, or a method of immersing a calcium solution and a phosphoric acid solution in alternately for a collagen or a collagen substrate, the control of a direction of an orientation or a degree of an orientation of the collagen substrate as used makes it possible to control a direction and a degree of an orientation of an orientated collagen/apatite material.

An orientated collagen/apatite material obtained thus comprises a collagen, and an apatite having an orientation similar to or almost the same as a direction of an orientation of the collagen, the apatite is produced and fixed on the collagen, accurately on the collagen, on a surface and or inside of the collagen. That is, an orientated collagen/apatite material obtained of the present invention can be also obtained by a method of producing an orientated collagen/apatite material according to the present invention as mentioned above.

An orientated collagen/apatite material according to the present invention comprises a collagen having an orientation, and an apatite produced and fixed on the collagen, accurately on the collagen, on a surface and or inside of the collagen which has an orientation similar to or almost the same as a direction of an orientation of the collagen. In an preferable embodiment, the orientation is an uniaxial orientation, a spiral orientation, a double axis orientation, a two-dimensional orientation, a triaxial orientation, or a three-dimensional orientation. The preparation of a collagen or a substrate coated by the collagen having such various orientation makes it possible to produce and fix an apatite having an orientation similar to or almost the same as a direction of an orientation of the collagen on the collagen, on a surface and/or inside of the collagen. The deposition of an apatite on the collagen, on a surface and/or inside of the collagen makes it possible to cause a calcification as mentioned above. Therefore, in a preferable embodiment, an orientated collagen/apatite material of the present invention is characterized in that a calcification occurs. An appearance of such a calcification makes it possible to produce a similar structure of a bone, and further the calcification makes it possible to increase an intensity (for example, it's intensity is clear in the case that it is clipped with a tweezer), and therefore, it has an advantage in the case that it is installed into an organism. Moreover, an orientated object as a calcific substance according to the prior art is those of an atelocollagen wherein an apatite is just orientated self-organizationally, and does not those of being produced and fixed an apatite having an orientation similar to or almost the same as a direction of an orientation of a collagen, on the surface and/or inside of a collagen. On the other hand, in the present invention, under the conditions that an atelocollagen is orientated, with the use of the orientated atelocollagen as a template, it is calcified and orientated. That is, those of the prior art is thought that it is as close as those of being each yarn staining and being fixed disorderly without no consideration of a direction of an yarn, assuming that a collagen is as an yarn and a deposition of an apatite is as a staining while, those of the present invention is thought that an yarn is packed into a bundle in one direction (for example, it means that it is orientated in one direction), and thereby staining each yarn to obtain those having an uniform direction of an yarn after construction. Therefore, although a various complex material is investigated in the prior art, there are no approaches of focusing an attention on an orientation in order to obtain a structure similar to or almost like those of an actual bone tissue, and thereby producing an fixing an apatite having an orientation similar to or the same as a direction of an orientation of collagen, on the surface and/or inside of a collagen as mentioned in the present invention.

Furthermore, in a preferred embodiment of an orientated collagen/apatite material according to the present invention, is characterized in that a size of the material is a macro size of a millimeter order or more. Furthermore, in a preferred embodiment of an orientated collagen/apatite material according to the present invention, is characterized in that the collagen having an orientation is coated on a substrate comprising a metal, a ceramics, a high-polymer material or a biomaterial. Moreover, a method of coating is not particularly limited to, but it depends on a common method.

EXAMPLE

At this moment, the present invention will be concretely explained in more detail with reference to Examples, but the invention is not intended to be interpreted as being limited to Examples. Moreover, it is possible to change appropriately without departing from the scope of the invention.

Example 1

In a method of the present invention, first of all, a collagen gel was prepared as an orientated collagen (substrate) having a size of a millimeter order or more. As to a collagen gel, 9.3 mg/mL concentration of I type of collagen solution derived from a rat tail (BD Company) was extruded through a nozzle having 0.38 mm of an inside diameter into a plate container containing a phosphate buffered saline (PBS) at 38° C., at pH7.4, and thereby sliding the nozzle to obtain a string like collagen gel having about 1 mm in diameter, about 20 mm of length. FIG. 1 gives a photograph of a collagen gel having an orientation immediately after it is produced in a PBS.

Figures 2, 3:
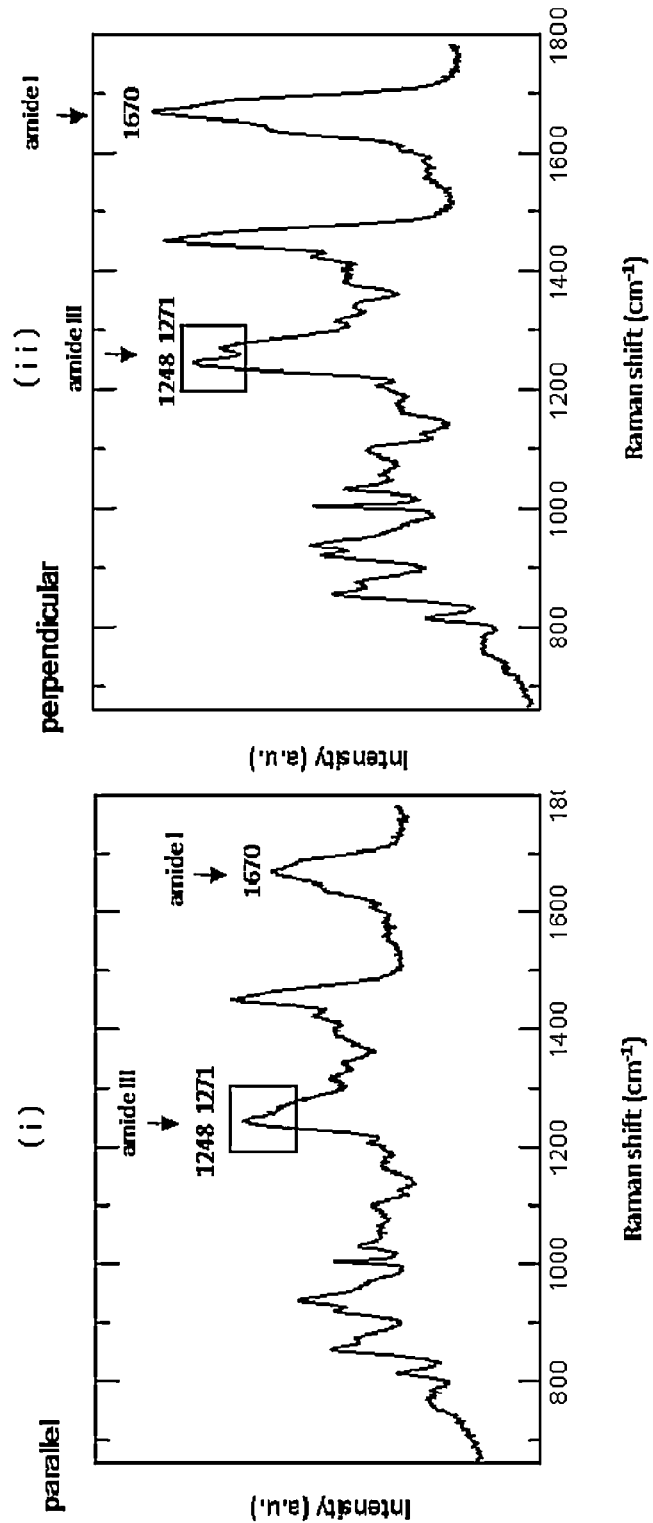
FIG. 2 gives a raman spectrum of an orientated collagen, (i) shows a spectrum in the case that a direction of a laser polarization is in parallel with a travel direction of a collagen, (ii) shows a spectrum in the case that a direction of a laser polarization is perpendicular to a travel direction of a collagen, respectively.
FIG. 3 gives a photograph of a result of an alizarin red S stain showing a calcification of a string like collagen gel.
Figure 3:
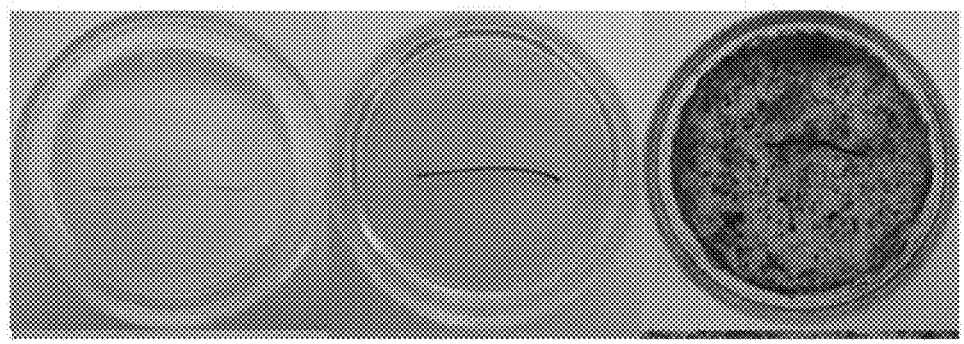

An orientation of a collagen gel obtained thus was analyzed by a raman spectroscopic microscope (PHOTON Design Corporation). In doing so, an excitation wavelength was set at 514.5 nm using a continuous oscillation argon ion laser Stabilite 2017 (Spectra-Physics, Inc.), a HR-320 (Jovin Yvon S.A.S.) as a spectroscope and a LN/CCD-1100-PB/UV AR/1 (Roper scientific Inc.) were used respectively. FIG. 2 gives a result of evaluating a strength of an amide I and an amide III in the case that a direction of a laser polarization is in parallel with and is perpendicular to a travel direction of a collagen. A peak derived from an amide I depends on a vibration of a C=O bonding located in a direction which is perpendicular to a collagen fiber, and a peak derived from an amide III depends on a vibration of a C—N bonding located in a direction which is in parallel with and perpendicular to a collagen fiber. According to FIG. 2, as to a spectrum wherein a direction of a laser polarization is in parallel with a travel direction of a collagen, compared with a strength of a peak depending on a $CH_3$ bending vibration around 1450 $cm^{-1}$, a peak strength of amide I (1670 $cm^{-1}$) as to a perpendicular direction was higher than that of a parallel direction. Further, in a spectrum wherein a direction of a laser polarization is perpendicular to a travel direction of a collagen, a peak of a vibration depending on a C—N bonding located in a direction perpendicular to a collagen fiber was observed around raman shift, 1270-1300 $cm^{-1}$. That is, it was recognized that a collagen fiber was oriented to a long axes direction of a collagen gel.

For a string like orientated collagen gel obtained thus, by seeding an osteoblast according to the following method, an apatite having an orientation similar to or almost the same as a direction of an orientation of the collagen (substrate) on a surface and/or inside of the collagen (substrate) was produced and fixed at a macro size of a millimeter order or more.

As an osteoblast, a mouse (in 0-2 days of life) calvaria original osteoblast was used, and a culture medium was MEM-α+10% of a bovine fetal blood serum, 100 U/mL of penicillin, 100 μg/mL of streptomycin, and thereby culturing for 1 week, and after that, by the use of a medium containing a MEM-α+10% of a bovine fetal blood serum, 100 U/mL of penicillin, 100 μg/mL of streptomycin+50 μg/mL of ascorbic acid+10 mm of β-glycerophosphoric acid+50 nM of dexamethasone, it was cultured for 3 weeks. The culture medium was changed at two times a week. A degree of density of a seeding is $2×10^4$/mL, it was carried out under the condition at 37° C., in 5% of $CO_2$. 35 mm of polystyrene dish was used as a culture dish. FIG. 3 gives a photograph of a result of an alizarin red S stain. An alizarin red stains a calcium salt utilizing a property which bonds to a metal. Therefore, it is possible to label a calcification of a collagen. From FIG. 3, it is recognized that a calcification of a string like collagen gel proceeds depending on the time of the culture.

Figure 4:
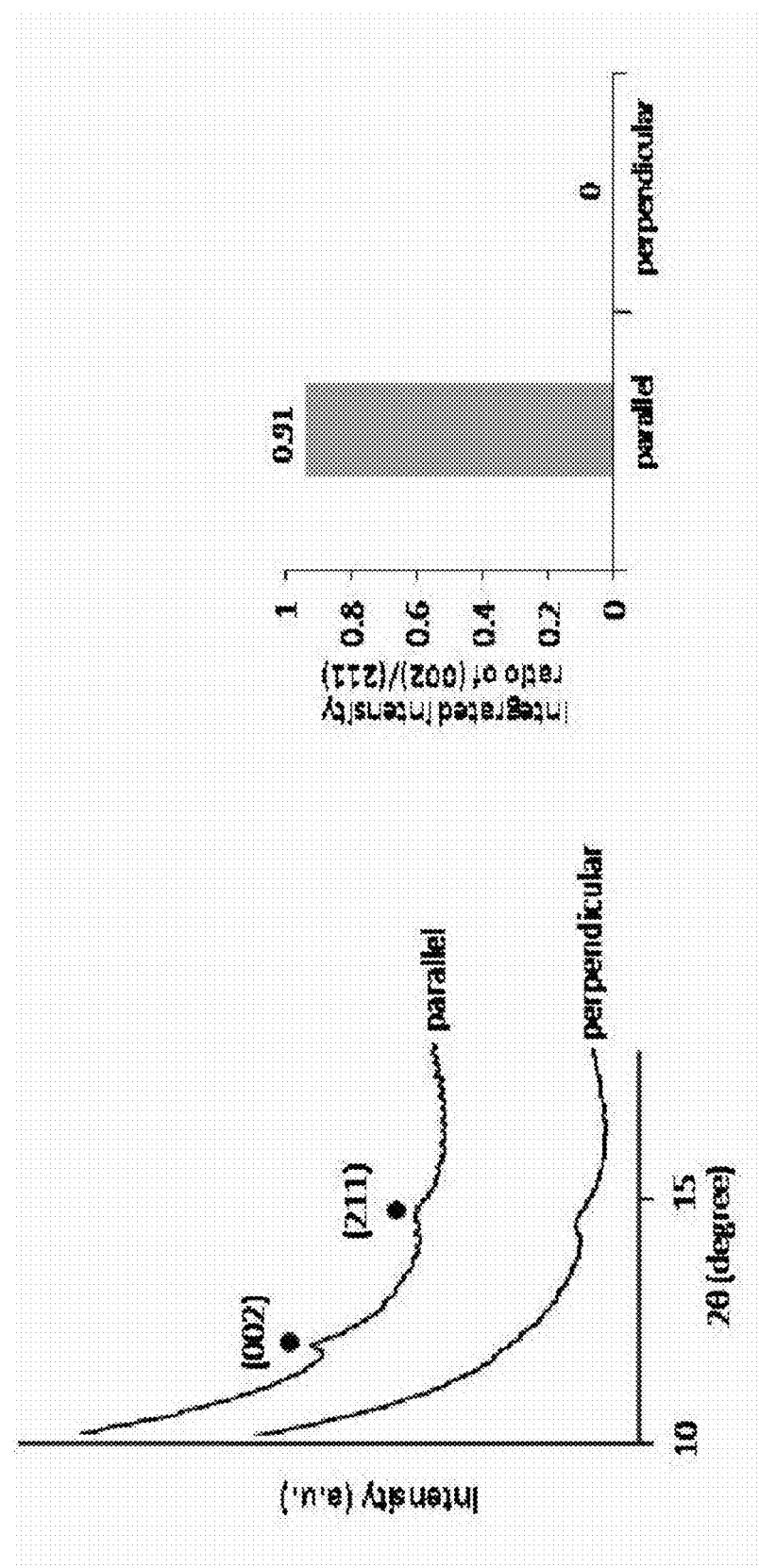
FIG. 4 gives a result of a X-ray diffraction of a collagen substrate 4 weeks after culturing.

Further, FIG. 4 gives a result of a X-ray diffraction of an orientated collagen/apatite material 4 weeks after culturing. In the X-ray diffraction, a transmission micro area X-ray diffractometer (R-AXIS BQ, Rigaku Co., Tokyo, Japan) was used, it was carried out under the conditions that a radiation source was a Mo-Kα (λ=0.07107 nm), a X-ray tube voltage was 50 kV, a X-ray tube current was 90 mA, a collimator was φ300 μm, an exposure time was 1200 seconds. From FIG. 4, although an integration ratio of a strength (002)/(211) was used as a standard of an orientation regarding a parallel direction and a perpendicular direction for a travel direction of a collagen fiber, it was recognized that in a parallel direction for a travel direction of a collagen fiber, a (002) plane was extremely orientated. That is, it was possible to orientate c axis of an apatite on the orientated collagen (substrate).

Moreover, it was also confirmed that an osteoblast like cell and an osteoblast were arrayed on the line with an orientated direction of collagen existing on the orientated collagen.

Example 2

Next, for a collagen (substrate) having an orientation, an orientated collagen/apatite material was produced by a method of immersing the collagen into a calcium solution and phosphate solution alternately.

A string like orientated collagen gel obtained in Example 1 was immersed into 200 mM of $CaCl_2$/Tris-HCL aq., (pH7.4) as a calcium solution and 120 mM of $Na_2HPO_4$ aq., as phosphate solution, alternately. A detail process of alternate immersing is as follows.

A collagen (substrate) was immersed into 37° C. of calcium solution for 2 minutes, and after that, it was washed in an ultrapure water for 30 seconds, and followed by immersing into phosphate solution for 2 minutes to wash it in an ultrapure water for 30 seconds. As assuming that this is one cycle, 30 cycles were carried out.

In the analysis of an orientation of an orientated collagen/apatite material obtained thus, a transmission micro area X-ray diffractometer (R-AXIS BQ, Rigaku Co., Tokyo, Japan) was used, it was carried out under the conditions that a radiation source was a Mo-Kα ($\lambda$=0.07107 nm), a X-ray tube voltage was 50 kV, a X-ray tube current was 90 mA, a collimator was $\phi$800 μm, an exposure time was 1200 seconds.

Figure 5:
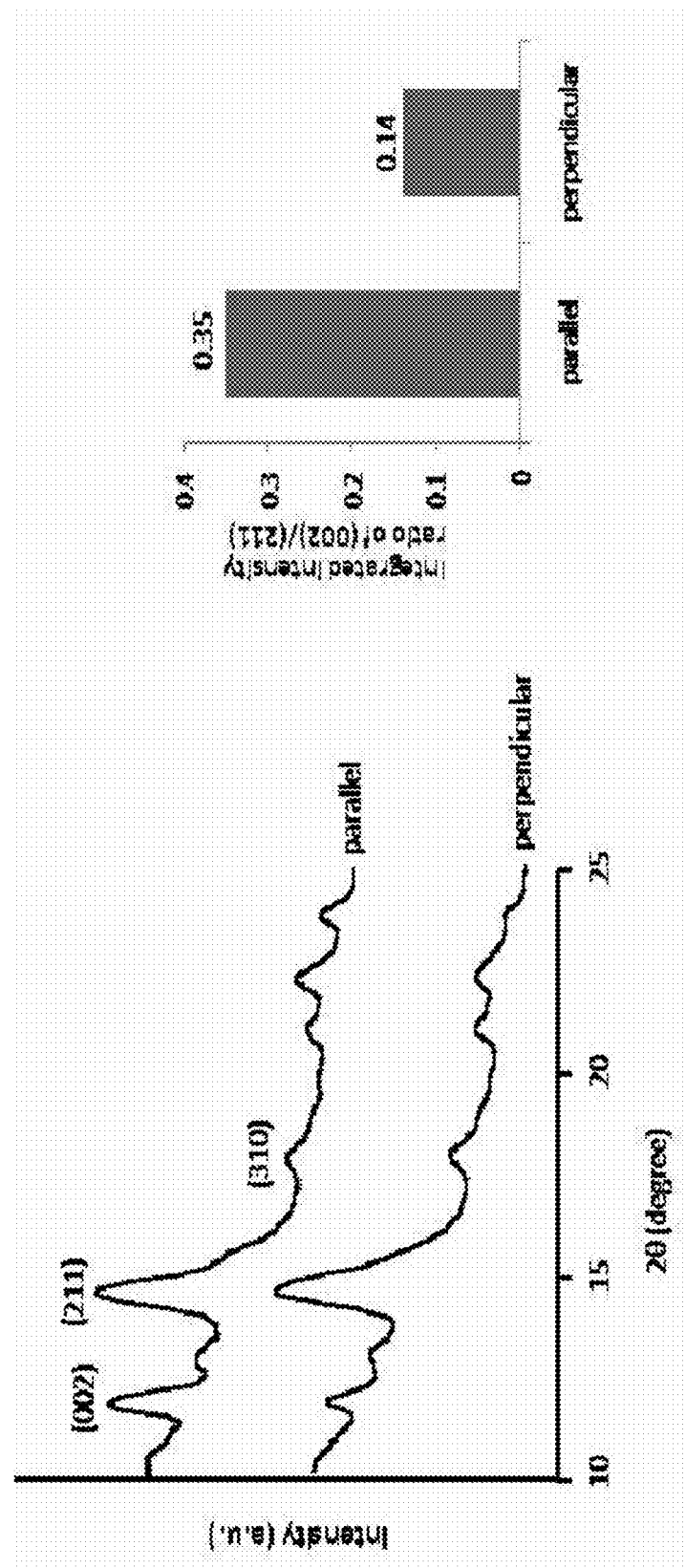
FIG. 5 gives a result of a X-ray diffraction of a collagen substrate after alternate immersion test at 30 times.

FIG. 5 gives a result of a X-ray diffraction (XRD)of an orientated collagen/apatite material after alternate immersion test at 30 times. From FIG. 5, although an integration ratio of a strength (002)/(211) was used as a standard of an orientation regarding a parallel direction and a perpendicular direction for a travel direction of a collagen fiber, it was recognized that in a parallel direction for a travel direction of a collagen fiber, a (002) plane was extremely orientated. That is, it was possible to orientate c axis of an apatite on the orientated collagen (substrate). That is, in an immersing process, a peak of XRD was confirmed ((002), (211), (310)) (a peak of an apatite), and thereby confirming a calcification.

INDUSTRIAL APPLICABILITY

The present inventions make it possible to contribute to a therapy directed at a disorder such as a bony defect of a tissue of a living organization such as a hard tissue of living body, for example, a born etc., a regenerative medicine and dental fields (in particular, orthopaedic surgery, a cerebral surgery, a medical dentistry) and basic medical fields

What is claimed is:

1. A method of producing an orientated collagen/apatite material consisting of:
    preparing a collagen having a controlled orientation, wherein the orientation is obtained by providing a flow of a fixed direction to a collagen solution during a process of gelating the collagen solution, which results in the oriented collagen; and
    performing 20-100 cycles of alternately immersing the oriented collagen into a solution containing calcium ion and a solution containing phosphate ion to produce and fix an apatite having an orientation wherein a direction of a C axis of the apatite is oriented in the direction of an orientation of the collagen on a surface and/or inside of the collagen, each of the cycles comprising:
    immersing the collagen into the solution containing the calcium ion;
    washing the collagen in water following the immersing the collagen into the solution containing the calcium ion;
    immersing the washed collagen into the solution containing the phosphate ion; and
    washing the collagen in water following the immersing the collagen into the solution containing the phosphate ion.

2. The method of producing an orientated collagen/apatite material according to claim 1, wherein the solution containing the phosphate ion is sodium hydrogenphosphate solution, sodium ammonium dihydrogenphosphate solution, tris buffer solution of sodium hydrogenphosphate, tris buffer solution of sodium ammonium dihydrogenphosphate or a mixed solution thereof.

3. The method of producing an orientated collagen/apatite material according to claim 1, wherein the solution containing the calcium ion is calcium chloride solution, calcium acetate solution, tris buffer solution of calcium chloride, tris buffer solution of calcium acetate or a mixed solution thereof.

4. The method of producing an orientated collagen/apatite material according to claim 3, wherein the solution containing the phosphate ion is sodium hydrogenphosphate solution, sodium ammonium dihydrogenphosphate solution, tris buffer solution of sodium hydrogenphosphate, tris buffer solution of sodium ammonium dihydrogenphosphate or a mixed solution thereof.

5. The method of producing an orientated collagen/apatite material according to claim 1, wherein the direction of the C axis of the apatite is oriented so that it is substantially the same as the direction of the orientation of the collagen on the surface and/or inside of the collagen.

6. The method of producing an orientated collagen/apatite material according to claim 1, wherein the washing the collagen in the water comprises washing the collagen in ultrapure water.

* * * * *